United States Patent
Weng et al.

(10) Patent No.: US 7,954,728 B2
(45) Date of Patent: Jun. 7, 2011

(54) METHOD FOR ADJUSTING AN OPERATION FREQUENCY AND CHECKING AN OPERATING STATE OF ULTRASONIC NEBULIZER

(75) Inventors: Shih-Yi Weng, Jinning Township, Kinmen County (TW); Yi-Hsin Huang, Taipei (TW); Shu-Mei Wu, Taipei (TW)

(73) Assignee: Taidoc Technology Corporation, Taipei (TW)

( * ) Notice: Subject to any disclaimer, the term of this patent is extended or adjusted under 35 U.S.C. 154(b) by 0 days.

(21) Appl. No.: 12/692,622

(22) Filed: Jan. 24, 2010

(65) Prior Publication Data

US 2010/0122696 A1 May 20, 2010

Related U.S. Application Data

(62) Division of application No. 11/626,832, filed on Jan. 24, 2007, now Pat. No. 7,673,812.

(51) Int. Cl.
*B05B 17/06* (2006.01)
*H02N 2/00* (2006.01)
*A61M 11/00* (2006.01)

(52) U.S. Cl. ............. 239/4; 239/102.1; 128/200.14; 128/200.16; 310/317

(58) Field of Classification Search ............ 239/4, 67, 239/69, 102.1, 102.2, 338; 128/200.14, 200.16; 310/316.01, 317
See application file for complete search history.

(56) References Cited

U.S. PATENT DOCUMENTS

| | | | | |
|---|---|---|---|---|
| 5,216,338 A | * | 6/1993 | Wilson | 318/116 |
| 5,551,416 A | * | 9/1996 | Stimpson et al. | 128/200.16 |
| 6,402,046 B1 | * | 6/2002 | Loser | 239/4 |
| 2002/0129813 A1 | * | 9/2002 | Litherland et al. | 128/200.16 |
| 2003/0164658 A1 | * | 9/2003 | Saraf | 310/317 |
| 2003/0196660 A1 | * | 10/2003 | Haveri | 128/203.12 |

* cited by examiner

*Primary Examiner* — Darren W Gorman
(74) *Attorney, Agent, or Firm* — Chun-Ming Shih

(57) ABSTRACT

A method for adjusting an operation frequency and checking an operating state of the ultrasonic nebulizer is related in the present invention. By detecting the current to determine a resonance frequency and whether deviated from a predetermined normal range, the nebulizer can check the operating state and operate at the resonance frequency for increasing efficiency and saving power.

9 Claims, 7 Drawing Sheets

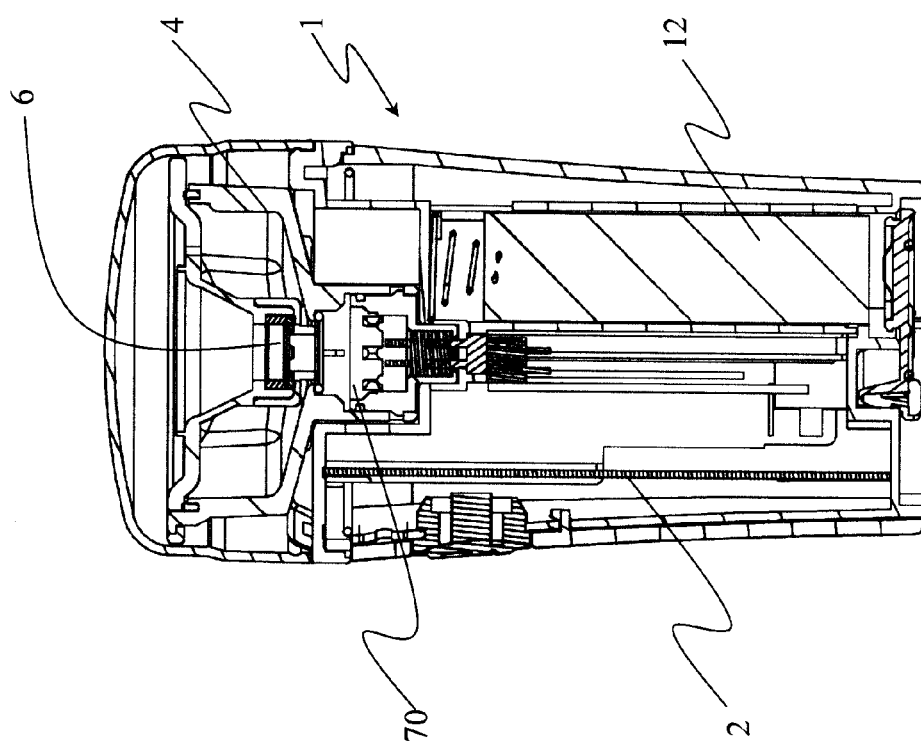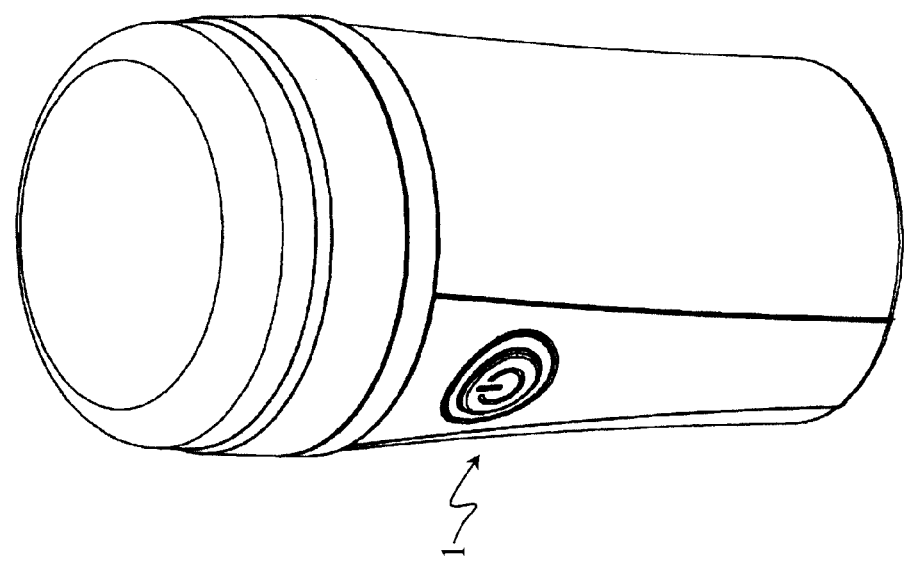

METHOD FOR ADJUSTING AN OPERATION FREQUENCY AND CHECKING AN OPERATING STATE OF ULTRASONIC NEBULIZER

This application is a divisional application of U.S. patent application Ser. No. 11/626,832, filed on Jan. 24, 2007 now U.S. Pat. No. 7,673,812.

BACKGROUND OF THE INVENTION

1. Field of the Invention

The present invention relates in general to an ultrasonic nebulizer apparatus. More particularly, the present invention relates to a portable ultrasonic nebulizer apparatus and a method for automatically adjusting an operating frequency and checking an operating state of the apparatus.

2. Description of the Related Art

Medical nebulizers that nebulize a fluid into a fine spray or aerosol for inhalation by a patient are well-known devices commonly used for the treatment of certain conditions and diseases. Persons requiring treatment of certain kinds of respiratory conditions frequently need to have medications delivered directly to the lungs. Since the lungs are close to the heart and the blood circulatory system of the body, drug administration by inhalation provides an effective delivery system to all organs of the body. Further, nebulizers have applications for conscious, spontaneously-breathing patients and for controlled, ventilated patients.

Effective and economical nebulizer therapy includes the ability to quickly generate a large amount of aerosol within a predetermined particle size range. There are several other considerations that relate to the effectiveness of nebulizer therapies. For example, it has been suggested that nebulization therapy is more effective when the generation of aerosol particles is relatively uniform.

In the recent years, the percentage of the chronic patients is increasing such that multiple therapies are required in home care, and therefore, portable ultrasonic nebulizers maybe available for such patients with time. In an ultrasonic nebulizer, the fine spray is produced by ultrasonic vibration of the liquid, as by a piezoelectric element. The liquid is dropped on, or otherwise applied to, the piezoelectric element. In addition, a specific characteristic of ultrasonic nebulizers is that the mechanical movement of the piezoelectric element may be tens or hundreds times higher at a mechanical resonance frequency compared with mechanical movement beyond the mechanical resonance frequency. It is a nonlinear mechanical movement of the piezoelectric element against the electrical signal frequency driving it. At the mechanical resonance frequency, and therefore, it is much more efficient to produce the vibrations to nebulize liquid.

Base on the above reason, conventional nebulizers set a constant frequency corresponding to a mechanical resonance frequency at that time when manufactured. However, many factors, such as variable environment temperature, usable in a period of time or changeable a part element of the nebulizer, will cause the mechanical resonance frequency displacement and alteration. As a result, the real time mechanical resonance frequency is changed timely dependent on the variable factors and will not maintain in a constant value so as to cause the mechanical movement of the piezoelectric element outside of the maximum movement. Conventional solving method is to send the nebulizer to the original manufactory or call a maintenance worker coming in a period of time for calibration and adjusting the operation frequency corresponding to the mechanical resonance frequency. There is a checking table for maintenance worker to detect and adjust some factors which will influence the operation frequency and then the worker will send the nebulizer back to owners. It wastes time and is so inconvenient for sending to and fro of the nebulizer or calling the maintenance worker coming.

Besides, if the liquid received in the nebulizer is insufficient or will be completely sprayed, the conventional nebulizer will not detect this situation and keep going for vibrating. Furthermore, at another abnormal situation, for example, a cover for protecting the liquid is removed, a part element of the apparatus is not connecting finely or a short circuit is occurred will not be detected. It means that when the conventional nebulizer is in an erroneous state, the nebulizer will not turn off itself. Further, a power saving of a portable apparatus is an important issue and then how to solve this problem is worth considering. Thus, a need exists for improved nebulizer.

SUMMARY OF THE INVENTION

According to one aspect of the present invention is to provide a portable ultrasonic nebulizer apparatus for automatically adjusting an operation frequency of the apparatus corresponding to a resonant frequency. In a preferred embodiment of the present invention, the portable ultrasonic nebulizer apparatus comprises:

a power supply for supplying power;

a vibrating element to vibrate a liquid to form an aerosol of fine droplets;

a variable oscillator for providing a plurality of frequencies to the vibrating element so as to let the vibrating element vibrates at the plurality of frequencies;

a step-up converter electrically connected with the variable oscillator for converting an input voltage to a boosted voltage to the vibrating element;

a current detecting element positioned between the power supply and the vibrating element for detecting an electrical current passing before the vibrating element and respectively corresponding to each of the plurality of frequencies; and a microprocessor for receiving the electrical current corresponding to each of the plurality of frequencies so as to determine the resonant frequency at which the electrical current is a maximum value and adjusting the operation frequency of the vibrating element provided by the variable oscillator corresponding to the resonant frequency.

Preferably, the step-up converter is a step-up DC-DC converter or a step-up DC-AC converter. More preferably, the apparatus in accordance with the present invention further comprises a single-phase alternating current supply electrically connected with the step-up converter and the vibrating element for providing the single-phase alternating current to the vibrating element.

Further, the vibrating element of the apparatus in accordance with the present invention preferably is a piezoelectric chip. The current detecting element may comprise a resistor for detecting a difference voltage between two sites between the resistor. In addition, the variable oscillator preferably comprises a digital resistor for providing a plurality of frequencies.

Furthermore, according to another aspect of the present invention is to provide a method for automatically adjusting an operation frequency to a resonant frequency of an ultrasonic nebulizer apparatus having a vibrating element to atomize a liquid into an aerosol of fine droplets, the method comprising:

providing a plurality of frequencies to the vibrating element;

detecting an electrical current passing through a current detecting element respectively corresponding to each of the plurality of frequencies, wherein the current detecting element is positioned before the vibrating element and actively detecting the electrical current;

determining a resonant frequency at which the corresponding measured current is a maximum value; and adjusting the operation frequency of the vibrating element corresponding to the resonant frequency.

Preferably, the method in accordance with the present invention further comprises shifting the apparatus to an adjusting mode before providing the plurality of frequencies to the vibrating element. More preferably, the plurality of frequencies is ranged from 180 to 200 kHz.

In addition, the current detecting element employed in the present invention comprises a resistor. More preferably, the plurality of frequencies is provided by a variable oscillator that comprises a digital resistor.

Preferably, the variable oscillator employed in the present invention is further connected with a step-up converter for supplying a boosted voltage to the vibrating element. More preferably, the step-up converter employed in the present invention is further connected with a single-phase alternating current supply for supplying a single-phase alternating current to the vibrating element.

According to another aspect of the present invention is to provide an ultrasonic nebulizer apparatus for automatically detecting an operating state of the apparatus, the apparatus comprising:

a power supply for supplying power;

a vibrating element to vibrate a liquid to form an aerosol of fine droplets;

a variable oscillator for providing an operation frequency to the vibrating element so as to let the vibrating element vibrates at the frequency;

a current detecting element positioned between the power supply and the vibrating element for measuring a current passing before the vibrating element and respectively corresponding to the frequency; and a microprocessor for receiving the current corresponding to the frequency so as to determine whether the current is deviated from a predetermined normal range.

Preferably, the apparatus according to the present invention further comprises a power switch positioned between the variable oscillator and the microprocessor for turning off the power supplied to the variable oscillator if the current is deviated from the predetermined normal range. More preferably, the apparatus further comprises a step-up converter positioned between the current detecting element and the vibrating element for providing a step-up power. Preferably, the step-up converter employed in the present invention is a step-up DC-DC converter.

The apparatus in accordance with the present invention may further comprise a single-phase alternating current supply positioned between the step-up DC-DC converter and the vibrating element for supplying a single-phase alternating current to the vibrating element. Preferably, the power switch employed in the present invention also positioned between the step-up DC-DC converter and the microprocessor for turning off the power supplied to the step-up DC-DC converter if the current is deviated from the predetermined normal range.

According to another aspect of the present invention is to provide a method for automatically detecting an operating state of an ultrasonic nebulizer, the method comprising:

providing an operation frequency to the vibrating element;

measuring a current passing through a current detecting element positioned before the vibrating element and respectively corresponding to the operation frequency; and determining the measured current whether deviated from a predetermined normal range.

Preferably, the method in accordance with the present invention further comprises turning off a power providing to the vibrating element if the measured current is deviated from the predetermined normal range.

According to another aspect of the present invention is to provide a portable ultrasonic nebulizer apparatus for automatically adjusting an operation frequency of the apparatus corresponding to a resonant frequency, comprising:

a power supply for supplying power;

a vibrating element to vibrate a liquid to form an aerosol of fine droplets;

a variable oscillator for providing a plurality of frequencies to the vibrating element so as to let the vibrating element vibrates at the plurality of frequencies;

a step-up converter electrically connected with the variable oscillator for converting an input voltage to a boosted voltage to the vibrating element;

a microprocessor for controlling the plurality of frequencies of the variable oscillator; and a current detecting element positioned between the vibrating element and the microprocessor for detecting an electrical current passing it and respectively corresponding to each of the plurality of frequencies;

wherein the microprocessor receives the electrical current corresponding to each of the plurality of frequencies so as to determine the resonant frequency at which the electrical current is a maximum value and adjusting the operation frequency of the vibrating element provided by the variable oscillator corresponding to the resonant frequency.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 is a perspective view of an ultrasonic nebulizer apparatus in accordance with the present invention;

FIG. 2 is a partial cross-sectional view of the nebulizer apparatus of FIG. 1;

DESCRIPTION OF THE PREFERRED EMBODIMENTS

Figure 3:
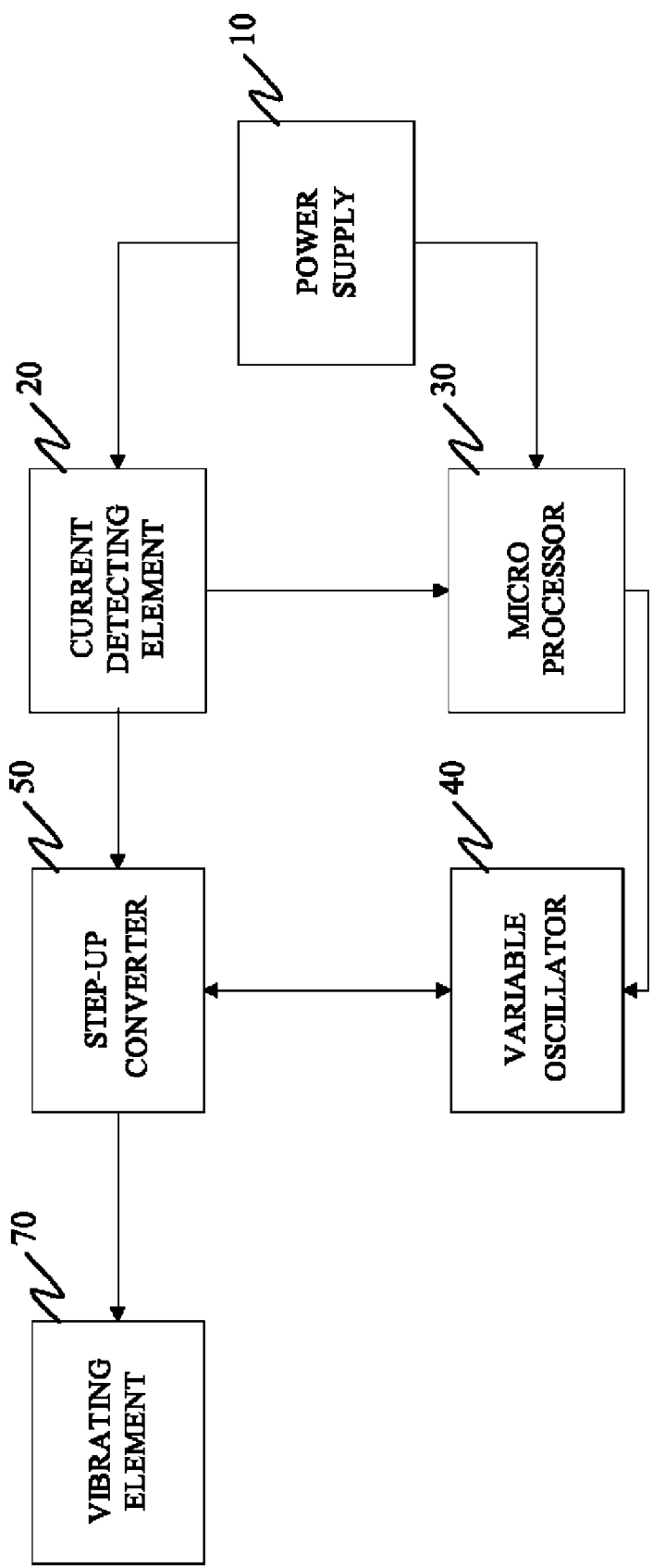
FIG. 3 is a preferred embodiment of a block diagram of the nebulizer apparatus of FIG. 1.
Figure 4:
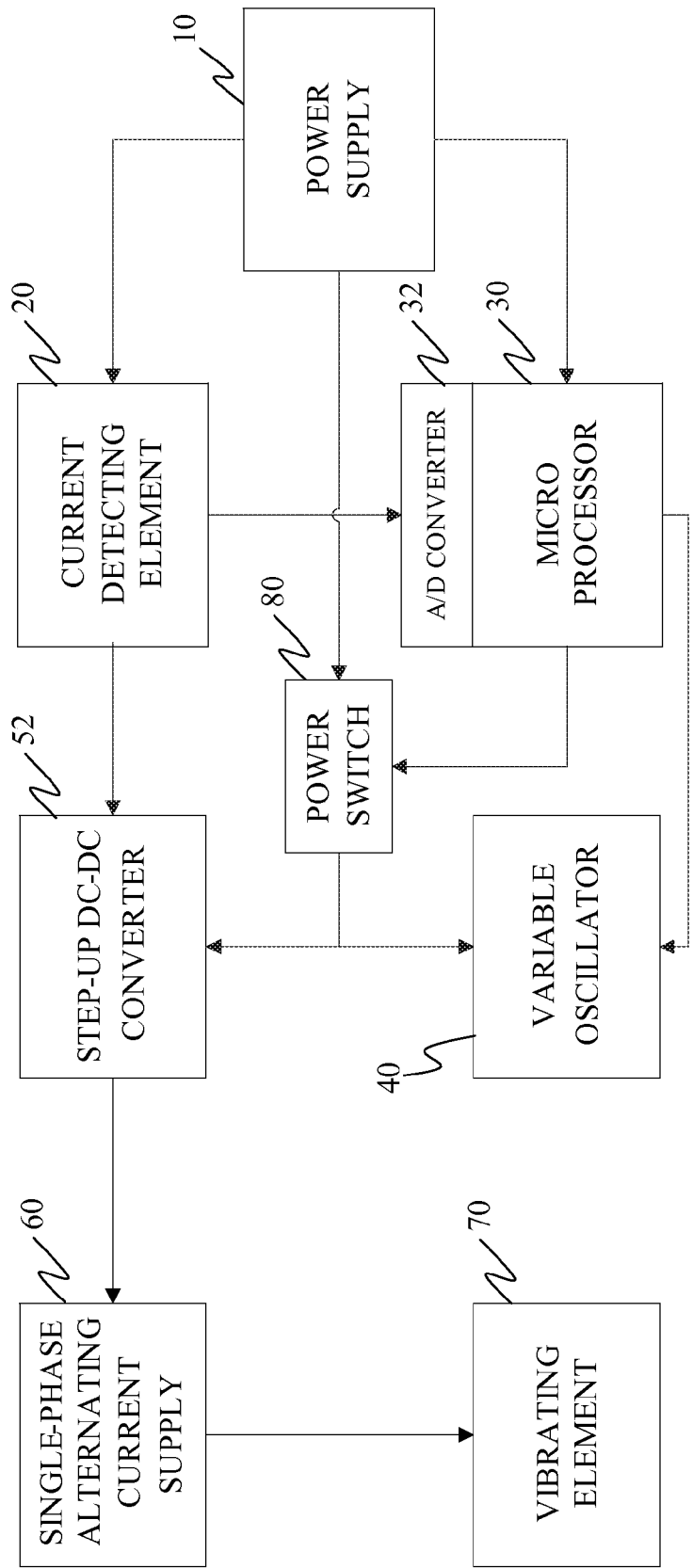
FIG. 4 is further preferred embodiment of a block diagram the nebulizer apparatus of FIG. 1.

With reference to FIGS. 1 to 3, a preferred embodiment of a portable ultrasonic nebulizer apparatus (1) in accordance with the present invention comprises a power supply (10), a circuit board (2), a vibrating element (70), a medication cup (4) and a mesh plate (6). In operation, a power is provided by the power supply (10) to the circuit board (2) for controlling the operation of the apparatus (1) and preferably, the power supply (10) may be a battery (12), as shown in FIG. 1, or a DC power. In a preferred embodiment, the battery (12) may be an "AA", "AAA", lithium-ion (Li-ion) or NiMH battery. In a further preferred embodiment, the DC power may be a transformer such as an AC to DC transformer. When a liquid, as like a pharmaceutical agent, an aqueous solution or suspended particulate, is received in the medication cup (4), the liquid is vibrated ultrasonically by the vibrating element (70) through the mesh plate (6) to nebulize the liquid. Preferably, the vibrating element (70) is a piezoelectric chip.

Figure 5:
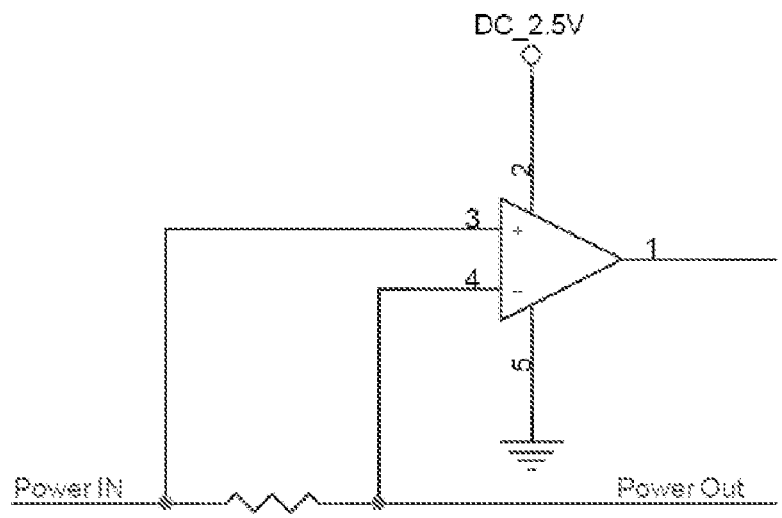
FIG. 5 is a circuit diagram of a current detecting element of the nebulizer apparatus of FIG. 1.

Referring now to FIG. 3, a block diagram of a preferred embodiment in accordance with the present invention shows a portable ultrasonic nebulizer apparatus comprises a power supply (10), a current detecting element (20), a microprocessor (30), a variable oscillator (40), a step-up converter (50) and a vibrating element (70). The power supply (10) applies DC power to the current detecting element (20) and the microprocessor (30). The current detecting element (20) detects an electrical current passed through it and then the microprocessor (30) receives the detected current signal. With further reference to FIG. 5, a preferred circuit diagram of the current detecting element (20) is shown. The current detecting element (20) referring to FIG. 5 comprises a resistor and detects the voltage difference between two sites across the resistor for calculating by the following equation:

$$I(\text{current}) = V(\text{voltage}) / R(\text{resistor})$$

Then, an electrical current is detected. By the current detecting element (20) coupled between the power supply (10) and the vibrating element (70), the microprocessor (30) can control the electrical current to a desired value before it passed to the vibrating element (70) for saving power by controlling the electrical current before the vibrating element (70). Otherwise, a conventional nebulizer detected a feedback signal of the vibrating element (70) for adjusting a small range voltage by analog adjusting method and thereby the conventional adjusting method can't be controlled before the vibrating element (70).

Further, a DC power is provided to the step-up converter (50) for converting an input voltage into a boosted output voltage whose value exceeds that of the input voltage. The step-up converter (50) comprises an inductance in a preferred embodiment and the principle is well known in the prior art. In another preferred embodiment, the step-up converter (50) is a step-up DC-AC converter that converting an input DC voltage into a boosted output AC voltage and supplying to the vibrating element (70). Besides, the step-up converter (50) can store energy to provide higher voltage than the original for increasing efficiency and saving power. For example, the step-up converter (50) can convert a 3V voltage to a 9V voltage for preparing a further higher voltage output such as almost 60V whereby the energy can store for preventing from wasting.

Figure 6:
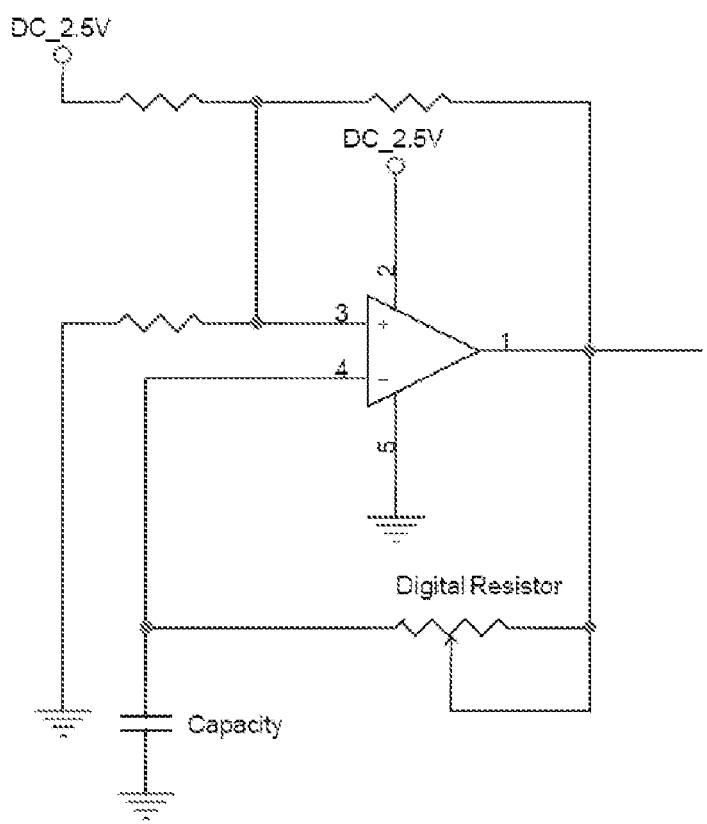
FIG. 6 is a circuit diagram of a variable oscillator of the nebulizer apparatus of FIG. 1.
Figure 7:
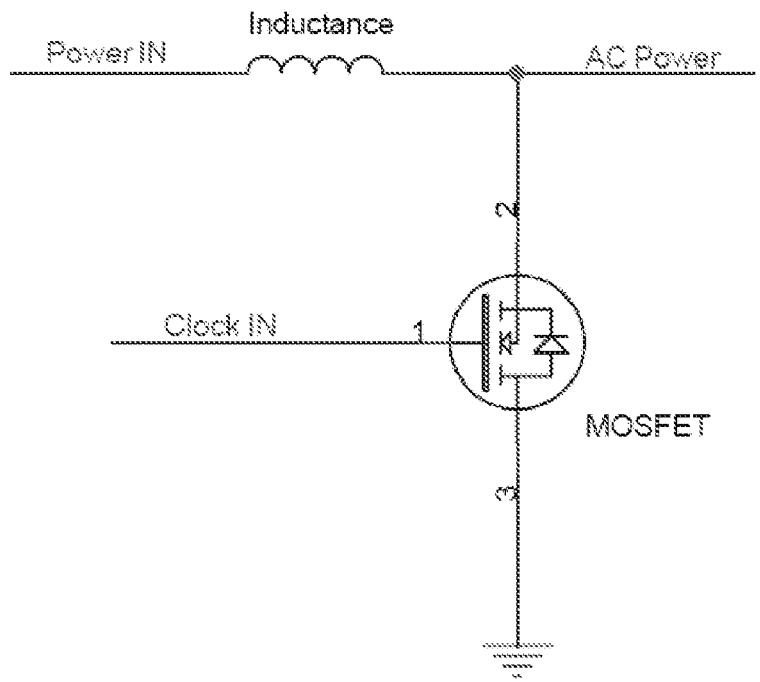
FIG. 7 is a circuit diagram of a single-phase alternating current supply of the nebulizer apparatus of FIG. 1.
Figure 8:
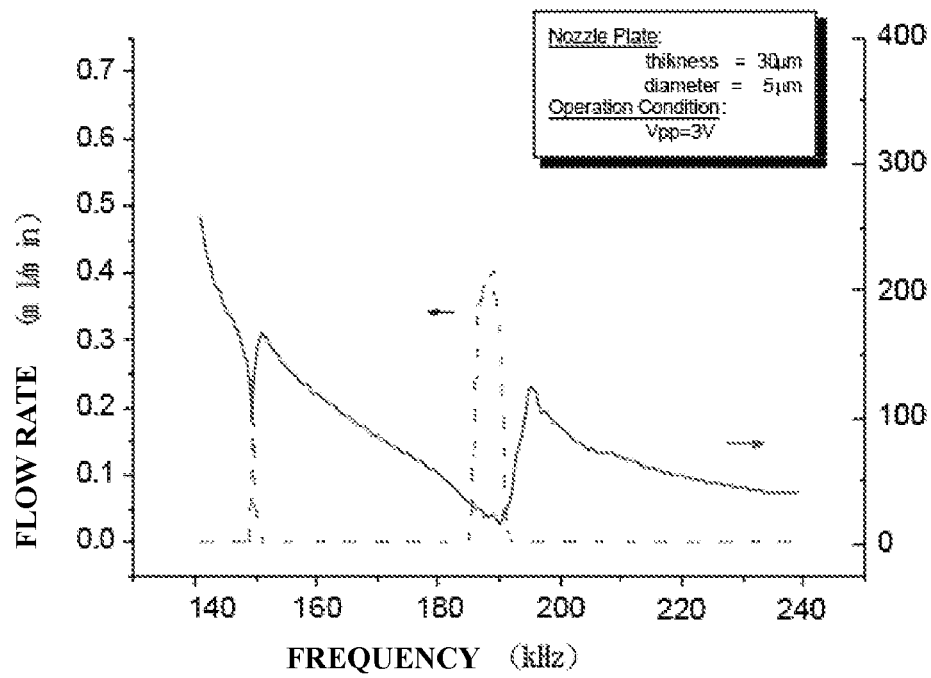
FIG. 8 is a schematic view representing electrical properties of a vibrating element.

The microprocessor (30) controls the variable oscillator (40) for providing variable frequencies to the step-up converter (50) and the vibrating element (70) and thereby the vibrating element (70) vibrates a liquid to form an aerosol of fine droplets. As further reference to FIG. 6, a preferred circuit diagram of the variable oscillator (40) is shown. The variable oscillator (40) preferably comprises a digital resistor for adjusting the time of charge and discharge. The variable oscillator (40) optionally further comprises a capacity whereby the frequency is produced by the following equation:

$$F(\text{frequency}) = 1/R(\text{resistor}) * C(\text{capacity})$$

By the digital resistor for adjusting the frequency, it has a broader bandwidth of the adjusting frequency, such as 180 to 200 mA, and further can control a change of the electrical current to the desire compared with a conventional method by analog adjusting the frequency. For example, the conventional analog adjusting method may only have an adjusting frequency range from 189.5 to 190.5 mA by adjusting voltage in a small range. In addition, the digital adjusting method has a broader tolerance range of the error of a plurality of electrical components.

According to FIG. 4, a further block diagram of a preferred embodiment of the portable ultrasonic nebulizer apparatus in accordance with the present invention is showing. The apparatus further comprises a single-phase alternating current supply (60) preferably. The single-phase alternating current supply (60) provides a single-phase alternating current to the vibrating element (70). Referring to FIG. 7, a preferred circuit diagram of the single-phase alternating current supply (60) is shown. The single-phase alternating current supply (60) comprises a MOSFET and an inductance. The electrical current will be changed by the provided frequency to apply a single-phase alternating current. The inductance is used for storage and release the passed energy. As a result, the single-phase alternating current will achieve the power saving advantage.

In a preferred embodiment, the current detecting element (20) may be positioned before the variable oscillator (40), the step-up converter (50), the single-phase alternating current supply (60) or the vibrating element (70). In addition, the current detecting element (20) may be positioned after the vibrating element (70) and between the vibrating element (70) and the microprocessor (30). If the current detecting element (20) is positioned between the vibrating element (70) and the microprocessor (30), the current detecting element (20) also can actively detect the electrical current passed through it and corresponding to the frequency and then the microprocessor (30) also can control the power switch (80) for turning off the power to the step-up DC-DC converter (52) and the variable oscillator (40).

With further reference to FIG. 8, a correlation between the frequency and the impedance is shown. The impedance of the vibrating element (70) is measured and provided through an analog/digital converter (32) to microprocessor (30) as shown in FIG. 4. To determine the resonance frequency of the vibrating element (70), the microprocessor (30) operates variable oscillator (40) to scan a predetermined frequency range in which the resonance frequency point should be found. The impedance of the vibrating element (70) is measured by the microprocessor (30) during the scanning to determine the foot value of the impedance that indicates the resonance frequency. At the foot value of the impedance, the electrical current is a maximum value. The resonance frequency is stored in a memory in microprocessor (30). After the resonance frequency is found, the microprocessor (30) operates variable oscillator (40) to provide desired operation frequency, the resonance frequency.

Furthermore, a preferred embodiment of the portable ultrasonic nebulizer apparatus of the present invention further comprises a power switch (80) for controlling power on/off of the step-up converter, such as step-up DC-DC converter (52) and the variable oscillator (40). When a signal from the current detecting element (20) received by the microprocessor (30) is out of a predetermined range, the microprocessor (30) controls to close the power switch (80) for the step-up DC-DC converter (52) and the variable oscillator (40). For example, the following table is a preferred embodiment of variable detected current value correlated to the state of the apparatus.

| State of the apparatus | Detected current value |
|---|---|
| Connected without a load | About 90 mA |
| Connected with a load | About 120 mA |
| Out of a minimum resistor of the vibrating element | About 120 mA |
| At a minimum resistor of the vibrating element | About 300~600 mA |
| A cover for protecting a liquid is removed | About 120 mA |
| Liquid received within the apparatus is removed | About 120 mA |
| Short circuit | >600 mA |

In the preferred embodiment, a predetermined normal range of the detected current is about 300~600 mA. If a current detected by the current detecting element (20) is out of the range and thereby the microprocessor (30) will control to close the power switch (80) for interrupting the electrical connection between the power supply (10) and the step-up DC-DC converter (52) and the variable oscillator (40).

Figure 9:
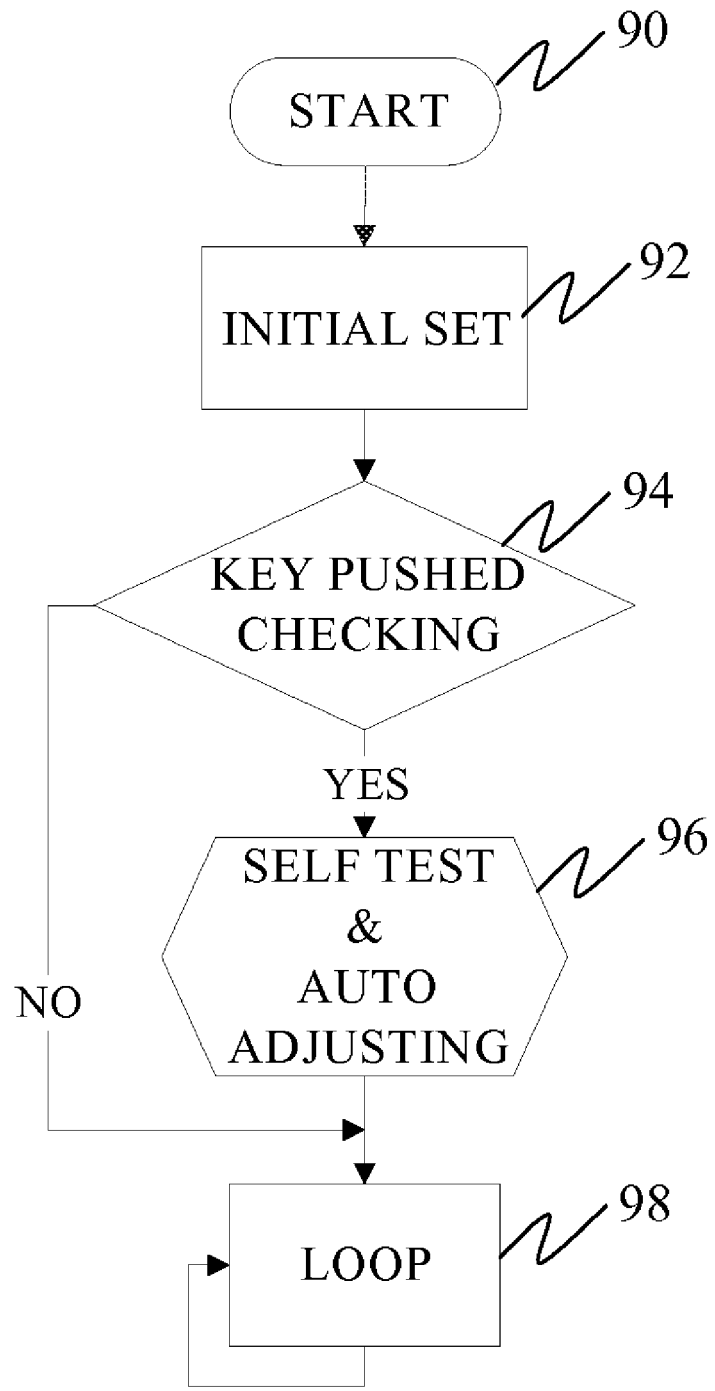
FIG. 9 is a preferred flow chart showing an adjusting operation step of the nebulizer apparatus of FIG. 1.

Further referring to FIG. 9, a flow chart shows an operation process for adjusting a frequency of the nebulizer apparatus in accordance with an exemplary embodiment of the present invention. An adjusting operation process is initiated at the START step (90) and proceeds to an initial set step (92). The START step (90) is started when a DC or battery put in. In the initial set step (92), the microprocessor (30) is set for preparing following-up operation. In checking step (94), the microprocessor (30) is checking whether or not a key is pushed. Preferably, the key is a power key. If the response to this inquiry is positive, the "YES" branch is followed to step (96). For example, a self test and auto adjusting is opened when the DC or battery put in and the power key is pushed. A negative response to this inquiry results in the process following the "NO" branch from step (94) to step (98). For example, if the DC or battery put in but the power key is not pushed, the operation is jumping to a loop and not to proceed the self test and auto adjusting.

Figure 10:
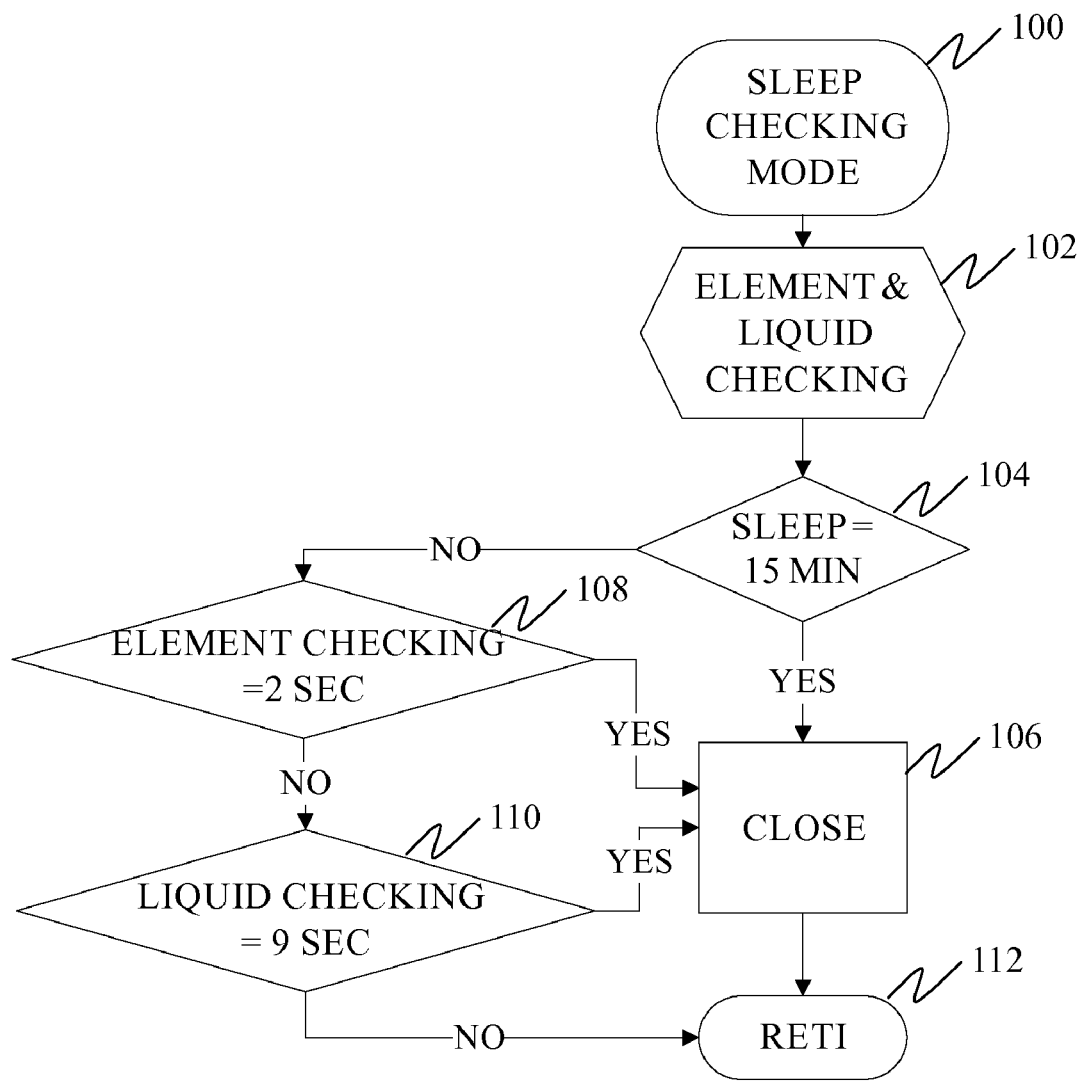
FIG. 10 is a preferred flow chart illustrating a method of checking an operating state of the nebulizer apparatus of FIG. 1.

According to FIG. 10, a preferred flow chart illustrates an operation step for checking an operating state of the nebulizer apparatus in accordance with the present invention. A sleep checking mode process (100) is initiated to a checking step (102) and proceeds to checking whether or not sleep=15 minutes (104). If the response to this inquiry is positive, the "Yes" branch is followed to step (106) for closing the apparatus. A negative response to this inquiry results in the process following the "No" branch from step (104) to step (108). In step (108), an element checking proceeded is made in 2 seconds for checking whether any element is in an abnormal operating state or not. If the element is in an abnormal operating state, the "Yes" branch is followed to step (106) and the apparatus is closed. The element checking step (108) is checking whether any element of the apparatus is removed or packed incompletely. Otherwise, the "No" branch is followed to step (110) for liquid checking. In step (110), a determination is made in 9 seconds for checking whether the liquid is in an abnormal operating state or not. If the liquid is in an abnormal operating state, the "Yes" branch is followed to step (106) and the apparatus is closed. The liquid checking step (110) checks whether the liquid received in the apparatus is vibrated completely or not. Otherwise, the "No" branch is followed to step (112). In step (112), the apparatus will return to a main program to proceed.

The nebulizer apparatus in accordance with the present invention has following advantages.

1. Automatically adjust an operation frequency of the nebulizer apparatus according to the present invention corresponding to a resonance frequency for achieving best vibrating efficiency.

2. Automatically check an operating state of the neulizer apparatus according to the present invention for preventing from occurring accident and achieving a safe and savable situation.

3. Providing a current detecting element to actively detect an electrical current passed through it and corresponding to a frequency for adjusting an operation frequency and controlling electrical current early.

4. By setting a step-up converter for supplying a boosted voltage thereby saving power and increasing efficiency.

5. Set a power switch between the power supply and the vibrating element for saving power when the apparatus is in an error operating state.

6. By setting a variable oscillator comprising a digital resistor for providing a variable frequency which can adjust a broader range of current to increase efficiency than an analog adjusting method for adjusting a narrower range of voltage.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. A method for automatically adjusting an operation frequency to a resonant frequency of an ultrasonic nebulizer apparatus having a vibrating element to atomize a liquid into an aerosol of fine droplets, the method comprising:
    providing a plurality of frequencies to the vibrating element;
    detecting an electrical current passing through a current detecting element respectively corresponding to each of the plurality of frequencies, wherein the current detecting element is positioned before the vibrating element and actively detecting the electrical current;
    determining a resonant frequency at which the corresponding measured current is a maximum value; and
    adjusting the operation frequency of the vibrating element corresponding to the resonant frequency.

2. The method as claimed in claim 1 further comprising shifting the apparatus to an adjusting mode before providing the plurality of frequencies to the vibrating element.

3. The method as claimed in claim 1, wherein the plurality of frequencies is ranged from 180 to 200 kHz.

4. The method as claimed in claim 1, wherein the current detecting element comprises a resistor.

5. The method as claimed in claim 1, wherein the plurality of frequencies is provided by a variable oscillator that comprises a digital resistor.

6. The method as claimed in claim 5, wherein the variable oscillator is further connected with a step-up converter for supplying a boosted voltage to the vibrating element.

7. The method as claimed in claim 6, wherein the step-up converter is further connected with a single-phase alternating current supply for supplying a single-phase alternating current to the vibrating element.

8. A method for automatically detecting an operating state of an ultrasonic nebulizer having a vibrating element to atomize a liquid into an aerosol of fine droplets, the method comprising:

provided an operation frequency to the vibrating element;

measuring a current passing through a current detecting element positioned before the vibrating element and corresponding to the operation frequency; and determining the measured current whether deviated from a predetermined normal range.

9. The method as claimed in claim 8 further comprising turning off a power providing to the vibrating element if the measured current is deviated from the predetermined normal range.

* * * * *